(12) United States Patent
Castro Pineiro et al.

(10) Patent No.: US 7,435,748 B2
(45) Date of Patent: Oct. 14, 2008

(54) GAMMA-SECRETASE INHIBITORS

(75) Inventors: Jose Luis Castro Pineiro, Bishops Stortford (GB); Ian James Collins, Redhill (GB); Timothy Harrison, Great Dunmow (GB)

(73) Assignee: Merck Sharp & Dohme Ltd., Hoddesdon, Hertfordshire (GB)

( * ) Notice: Subject to any disclaimer, the term of this patent is extended or adjusted under 35 U.S.C. 154(b) by 0 days.

(21) Appl. No.: 11/639,089

(22) Filed: Dec. 14, 2006

(65) Prior Publication Data

US 2007/0088063 A1    Apr. 19, 2007

Related U.S. Application Data

(63) Continuation of application No. 10/982,586, filed on Nov. 5, 2004, now Pat. No. 7,183,303.

(30) Foreign Application Priority Data

Nov. 7, 2003    (GB) ................................. 0326039.5

(51) Int. Cl.
*A61K 31/427*    (2006.01)
(52) U.S. Cl. ........................ 514/340; 514/363; 514/364; 514/365; 514/372
(58) Field of Classification Search ................. 514/340, 514/363, 364, 365, 372
See application file for complete search history.

(56) References Cited

FOREIGN PATENT DOCUMENTS

WO    WO 01/70677    9/2001
WO    WO 02/36555    5/2002

OTHER PUBLICATIONS

M. N. Pangalos et al., "Disease modifying strategies for the treatment of Alzheimer's disease targeted at modulating levels of the beta-amyloid peptide", Biochemical Society Transactions, vol. 33, Part 4, pp. 553-558 (2005).

I. Churcher et al., "Gamma-Secretase as a Therapeutic Target for the Treatment of Alzheimer's Disease", Current Pharmaceutical Design, vol. 11, pp. 3363-3382 (2005).
D. M. Barton et al., "Dynamics of Beta-Amyloid Reductions in Brain, Cerebrospinal Fluid and Plasma of Beta-Amyloid Precursor Protein Transgenic Mice Treated with a gamma-secretase Inhibitor", JPET, vol. 312, No. 2, pp. 635-643 (2005).
E. R. Siemers et al., "Effects of a gamma-secretase inhibitor in a randomized study of patients with Alzheimer disease", Neurology, vol. 66, pp. 602-604 (2006).
G. Evin et al., "Inhibition of gamma-secretase as a Therapeutic Intervention for Alzheimer's Disease", CNS Drugs, vol. 20, No. 5, pp. 351-372 (2006).
M. S. Shearman et al., "L-685,458, and Aspartyl Protease Transition State Mimic, Is A Potent Inhibitor of Amyloid Beta-Secretase Precursor gamma-secretase Activity", Biochemistry, vol. 39, pp. 8698-8704 (2000).
H. Josien, "Recent advances in the development of gamma-secretase inhibitors", Current Opinion in Drug Discovery & Development, vol. 5, No. 4, pp. 513-525 (2002).
M. S. Wolfe, "Secretase Targets for Alzheimer's Disease: Identification and Therapeutic Potential", J. Med. Chem., vol. 44, No. 13, pp. 2039-2060 (2001).
E. E. Clarke et al., "Quantitation of amyloid-beta peptides in biological milieu using a novel homogeneous time-resolved fluorescence (HTRF) assay", J. of Neuroscience Methods, vol. 102, pp. 61-68 (2000).

*Primary Examiner*—Kahsay T Habte
(74) *Attorney, Agent, or Firm*—William Krovatin; Raynard Yuro

(57) ABSTRACT

Compounds of formula I:

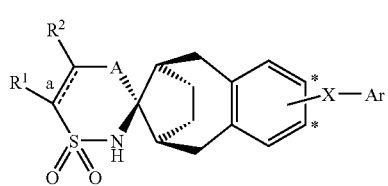

inhibit gamma-secretase and hence find use in treatment of Alzheimer's disease.

1 Claim, No Drawings

GAMMA-SECRETASE INHIBITORS

CROSS-REFERENCE TO RELATED APPLICATIONS

This application is a continuation of U.S. patent application Ser. No. 10/982,586, filed Nov. 5, 2004 now U.S. Pat. No. 7,183,303, which claims priority under 35 U.S.C. § 119(e) of Great Britain application no. 0326039.5, filed Nov. 7, 2003.

BACKGROUND OF THE INVENTION

The present invention relates to a novel class of compounds, their salts, pharmaceutical compositions comprising them, processes for making them and their use in therapy of the human body. In particular, the invention relates to novel sulphonamide derivatives which modulate the processing of APP by γ-secretase, and hence are useful in the treatment or prevention of Alzheimer's disease.

Alzheimer's disease (AD) is the most prevalent form of dementia. Although primarily a disease of the elderly, affecting up to 10% of the population over the age of 65, AD also affects significant numbers of younger patients with a genetic predisposition. It is a neurodegenerative disorder, clinically characterized by progressive loss of memory and cognitive function, and pathologically characterized by the deposition of extracellular proteinaceous plaques in the cortical and associative brain regions of sufferers. These plaques mainly comprise fibrillar aggregates of β-amyloid peptide (Aβ). The role of secretases, including the putative γ-secretase, in the processing of amyloid precursor protein (APP) to form Aβ is well documented in the literature and is reviewed, for example, in WO 01/70677.

There are relatively few reports in the literature of compounds with inhibitory activity towards □-secretase, as measured in cell-based assays. These are reviewed in WO 01/70677. Many of the relevant compounds are peptides or peptide derivatives.

WO 01/70677 and WO 02/36555 disclose, respectively, sulphonamido- and sulphamido -substituted bridged bicycloalkyl derivatives which are believed to be useful in the treatment of Alzheimer's disease, but do not disclose or suggest compounds in accordance with the present invention.

The present invention provides a novel class of bridged bicycloalkyl spirocyclic sulphonamide derivatives which show a particularly strong inhibition of the processing of APP by the putative □-secretase, and thus are useful in the treatment or prevention of AD.

According to the invention there is provided a compound of formula I:

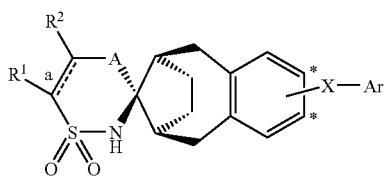

I wherein the moiety X—Ar is attached at one of the positions indicated by an asterisk;

X is a bivalent residue of a heteroaryl ring comprising 5 ring atoms of which two or three are selected from O, N and S, optionally bearing a hydrocarbon substituent comprising 1-5 carbon atoms which is optionally substituted with up to 3 halogen atoms;

Ar is phenyl or 6-membered heteroaryl, either of which bears 0-3 substituents independently selected from halogen, $CF_3$, $CHF_2$, $CH_2F$, $NO_2$, CN, $OCF_3$, $C_{1-6}$alkyl and $C_{1-6}$alkoxy;

A is $(CH_2)n$ where n is 0, 1 or 2;

bond a is single or double;

$R^1$ is H or $C_{1-6}$alkyl, $C_{2-6}$alkenyl, or $C_{2-6}$alkynyl, any of which optionally is substituted with up to 5 fluorine atoms; or $R^1$ and $R^2$ together complete a fused benzene ring which is optionally substituted with up to 3 halogen atoms or $C_{1-4}$alkyl groups; and $R^2$ is H or together with $R^1$ completes a fused benzene ring as described above;

or a pharmaceutically acceptable salt thereof.

It will be readily apparent to those skilled in the art that the compounds of formula I exist in two enantiomeric forms, depending on which of the ring positions indicated by an asterisk is bonded to the moiety —X—Ar. It is to be emphasised that the invention, for each identity of —X—Ar, encompasses both enantiomers, either as homochiral compounds or as mixtures of enantiomers in any proportion, although attachment at the position indicated by the upper asterisk is preferred. Furthermore, structural formulae depicting attachment of —X—Ar or a synthetic precursor thereof at one of the said ring positions shall hereinafter be indicative of attachment at either of said ring positions, unless expressly stated otherwise.

Where a variable occurs more than once in formula I or in a substituent thereof, the individual occurrences of that variable are independent of each other, unless otherwise specified.

As used herein, the expression "$C_{1-x}$alkyl" where x is an integer greater than 1 refers to straight-chained and branched alkyl groups wherein the number of constituent carbon atoms is in the range 1 to x. Particular alkyl groups are methyl, ethyl, n-propyl, isopropyl and t-butyl. Derived expressions such as "$C_{2-6}$alkenyl", "hydroxy$C_{1-6}$alkyl", "heteroaryl$C_{1-6}$alkyl", "$C_{2-6}$alkynyl " and "$C_{1-6}$alkoxy" are to be construed in an analogous manner. Most suitably, the number of carbon atoms in such groups is not more than 4.

The term "halogen" as used herein includes fluorine, chlorine, bromine and iodine, of which fluorine and chlorine are preferred.

For use in medicine, the compounds of formula I may be in the form of pharmaceutically acceptable salts. Other salts may, however, be useful in the preparation of the compounds of formula I or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, benzenesulphonic acid, fumaric acid, maleic acid, succinic acid, acetic acid, benzoic acid, oxalic acid, citric acid, tartaric acid, carbonic acid or phosphoric acid. Alternatively, where the compound of the invention carries an acidic moiety, a pharmaceutically acceptable salt may be formed by neutralisation of said acidic moiety with a suitable base. Examples of pharmaceutically acceptable salts thus formed include alkali metal salts such as sodium or potassium salts; ammonium salts; alkaline earth metal salts such as calcium or magnesium salts; and salts formed with suitable organic bases, such as amine salts (including pyridinium salts) and quaternary ammonium salts.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

In the compounds of formula I, X is a bivalent residue of a 5-membered heteroaryl ring as defined previously. Suitable heteroaryl rings include pyrazole, imidazole, triazole, oxazole, isoxazole, thiazole, isothiazole, thiadiazole and oxadiazole, optionally bearing a hydrocarbon substituent as defined previously. X may be bonded to Ar and to the fused benzene ring shown in formula I via any of the available ring positions of X. Typically, X is bonded both to Ar and to the fused benzene ring via carbon atoms, but when X is a pyrazole, imidazole or triazole residue, one of the points of attachment may be a nitrogen atom. Preferably, the points of attachment do not occupy adjacent ring atoms of X.

The ring represented by X optionally bears a hydrocarbon substituent comprising 1 to 5 carbon atoms, optionally substituted with up to 3 halogen atoms. Said optional hydrocarbon substituent may be attached to one of the ring carbon atoms of X, or when X is a pyrazole, imidazole or triazole residue and both of its points of attachment are carbon atoms, it may be attached to one of the ring nitrogen atoms of X. In either case, the optional hydrocarbon substituent may comprise cyclic or acyclic hydrocarbon residues or combinations thereof, saturated or unsaturated, up to a maximum of 5 carbon atoms in total. The optional hydrocarbon substituent is preferably unsubstituted or is substituted with up to 3 fluorine atoms Examples include methyl, ethyl, n-propyl, isopropyl, n-butyl, sec-butyl, t-butyl, fluoromethyl, difluoromethyl, trifluoromethyl, 2,2,2-trifluoroethyl, cyclopropyl, cyclopropylmethyl and allyl. A preferred example is methyl.

When X is a triazole, oxadiazole or thiadiazole residue, both of the possible isomeric forms are within the scope of the invention. Thus, the definition of X encompasses both 1,2,3- and 1,2,4-triazole residues, and both 1,2,4- and 1,3,4-thiadiazole residues, and both 1,2,4- and 1,3,4-oxadiazole residues.

Suitable identities for X include 1,3,4-oxadiazol-2-yl, 1,3,4-thiadiazol-2-yl, 1,3,4-triazol-2-yl, 1,2,3-triazol-4-yl, 1,2,3-triazol-1-yl, 1,2,4-triazol-3-yl, 1-methyl-1,2,4-triazol-3-yl, oxazol-2-yl, pyrazol-3-yl, 1-methylpyrazol-3-yl, 1-methylpyrazol-5-yl, 1-ethylpyrazol-3-yl, 1-(2,2,2-trifluoroethyl) pyrazol-3-yl, thiazol-2-yl, 4-methylthiazol-2-yl, isoxazol-2-yl, isoxazol-3-yl, imidazol-2-yl, imidazol-4-yl and imidazol-1-yl, wherein the numbering indicates the ring atom of X which is attached to the fused benzene ring in formula I.

Preferred identities for X include 1-methyl-1,2,4-triazol-3-yl, 1-methylpyrazol-3-yl, 1-ethylpyrazol-3-yl, oxazol-2-yl, thiazol-2-yl and 4-methylthiazol-2-yl, in which Ar is attached to the 5-position of X. A further preferred identity for X is imidazol-4-yl in which Ar is attached to the 1-position of X. Another preferred identity for X is 1,2,4-triazol-3-yl in which Ar is attached to the 1-position of X.

Particularly preferred identities for X are 1-methylpyrazol-3-yl in which Ar is attached to the 5-position and imidazol-4-yl in which Ar is attached to the 1-position.

Ar represents phenyl or 6-membered heteroaryl, either of which bears 0-3 substituents independently selected from halogen, $CF_3$, $CHF_2$, $CH_2F$, $NO_2$, CN, $OCF_3$, $C_{1-6}$alkyl and $C_{1-6}$alkoxy. Examples of suitable 6-membered heteroaryl groups represented by Ar include pyridyl, pyrazinyl, pyrimidinyl, pyridazinyl and triazinyl, of which pyridyl is preferred. Preferably, the phenyl or heteroaryl ring bears 0 to 2 substituents. Phenyl groups represented by Ar preferably bear at least one substituent. Preferred substituents include halogen (especially chlorine and fluorine), CN, $C_{1-6}$alkyl (especially methyl), $C_{1-6}$alkoxy (especially methoxy), $OCF_3$ and $CF_3$. If two or more substituents are present, preferably not more than one of them is other than halogen or alkyl. Examples of groups represented by Ar include phenyl, monohalophenyl, dihalophenyl, trihalophenyl, cyanophenyl, methylphenyl, methoxyphenyl, trifluoromethylphenyl, trifluoromethoxyphenyl, pyridyl, monohalopyridyl and trifluoromethylpyridyl, wherein "halo" refers to fluoro or chloro. Suitable specific values for Ar include 2-fluorophenyl, 2-chlorophenyl, 3-fluorophenyl, 4-fluorophenyl, 4-chlorophenyl, 2,4-difluorophenyl, 2,4-dichlorophenyl, 3,4-difluorophenyl, 3,4-dichlorophenyl, 3-chloro-4-fluorophenyl, 3,4,5-trifluorophenyl, 4-cyanophenyl, 4-methylphenyl, 4-methoxyphenyl, 2-(trifluoromethyl)phenyl, 4-(trifluoromethyl)phenyl, 4-(trifluoromethoxy)phenyl, pyridin-2-yl, pyridin-3-yl, pyridin-4-yl, pyrazin-2-yl, 5-methylpyridin-2-yl, 5-fluoropyridin-2-yl, 5-chloropyridin-2-yl, 5-(trifluoromethyl)pyridin-2-yl and 6-(trifluoromethyl)pyridin-3-yl. Preferred examples include 2-fluorophenyl, 2-chlorophenyl, 3-fluorophenyl, 4-fluorophenyl, 4-chlorophenyl, 2,4-difluorophenyl, 2,4-dichlorophenyl, 3,4-difluorophenyl, 3,4-dichlorophenyl, 3-chloro-4-fluorophenyl, 4-(trifluoromethyl)phenyl, pyridin-2-yl, pyridin-3-yl and pyridin-4-yl.

Particularly preferred identities of Ar—X—include 5-(4-chlorophenyl)-1-methylpyrazol-3-yl, 5-(4-fluorophenyl)-1-methylpyrazol-3-yl and 1-(4-fluorophenyl)imidazol-4-yl.

In formula I, A represents $(CH_2)n$ where n is 0, 1 or 2. Preferably, n is 0 or 1.

The bond a may be single or double. In one embodiment, when bond a is double, $R^1$ and $R^2$ are both H or else complete a fused benzene ring.

$R^1$ is H or $C_{1-6}$alkyl, $C_{2-6}$alkenyl, or $C_{2-6}$alkynyl, any of which optionally is substituted with up to 5 fluorine atoms; or $R^1$ and $R^2$ together complete a fused benzene ring as defined previously. Preferably $R^1$ is H, optionally-substituted $C_{1-6}$alkyl (such as methyl, ethyl, n-propyl, isopropyl, n-butyl or 2,2,2-trifluoroethyl), $C_{2-6}$alkenyl (such as allyl) or completes a fused benzene ring.

When $R^1$ and $R^2$ complete a fused benzene ring, said ring may be substituted with up to 3 halogen atoms (especially Cl or F) or $C_{1-4}$alkyl groups (especially methyl), but is preferably unsubstituted.

The compounds of the present invention have an activity as inhibitors of γ secretase.

The invention also provides pharmaceutical compositions comprising one or more compounds of this invention and a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, transdermal patches, auto-injector devices or suppositories; for oral, parenteral, intranasal, sublingual or rectal administration, or for administration by inhalation or insufflation. The principal active ingredient is mixed with a pharmaceutical carrier, e.g. conventional tableting ingredients such as corn starch, lactose, sucrose, sorbitol, talc, stearic acid, magnesium stearate and dicalcium phosphate, or gums or surfactants such as sorbitan monooleate, poly(ethylene glycol), and other pharmaceutical diluents, e.g. water, to form a homogeneous preformulation composition containing a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. Tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, liquid- or gel-filled capsules, suitably flavoured syrups, aqueous or oil suspensions, and flavoured emulsions with edible oils such as cottonseed oil, sesame oil or coconut oil, as well as elixirs and similar pharmaceutical vehicles. Suitable dispersing or suspending agents for aqueous solutions, gels or suspensions include synthetic and natural gums such as tragacanth, acacia, alginate, dextran, sodium carboxymethylcellulose, methylcellulose, poly(ethylene glycol), poly(vinylpyrrolidone) or gelatin.

The present invention also provides a compound of the invention or a pharmaceutically acceptable salt thereof for use in a method of treatment of the human body. Preferably the treatment is for a condition associated with the deposition of β-amyloid. Preferably the condition is a neurological disease having associated β-amyloid deposition such as Alzheimer's disease.

The present invention further provides the use of a compound of the present invention or a pharmaceutically acceptable salt thereof in the manufacture of a medicament for treating or preventing Alzheimer's disease.

Also disclosed is a method of treatment of a subject suffering from or prone to Alzheimer's disease which comprises administering to that subject an effective amount of a compound according to the present invention or a pharmaceutically acceptable salt thereof.

For treating or preventing Alzheimer's Disease, a suitable dosage level is about 0.01 to 250 mg/kg per day, preferably about 0.01 to 100 mg/kg per day, more preferably about 0.05 to 50 mg/kg of body weight per day, and for the most preferred compounds, about 0.1 to 10 mg/kg of body weight per day. The compounds may be administered on a regimen of 1 to 4 times per day. In some cases, however, a dosage outside these limits may be used.

The compounds of the invention are particularly suitable for oral administration.

Compounds of formula I may be prepared by coupling of compounds of formula II with compounds of formula III:

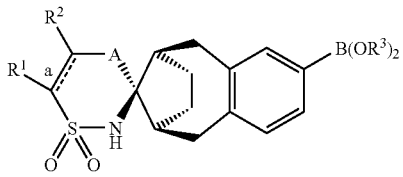

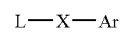

where $R^3$ represents H or alkyl, or the two $OR^3$ groups complete a cyclic boronate ester such as the pinacolate or the neopentyl glycolate, L is a suitable leaving group (such as halogen, especially bromine or iodine, triflate or nonaflate), and X, Ar, A, a, $R^1$ and $R^2$ have the same meanings as before. The reaction takes place in the presence of a Pd catalyst such as bis(diphenylphosphinoferrocene)dichloropalladium(II) or tetrakis(triphenylphosphine)palladium(0), typically in the presence of an inorganic base such as potassium acetate or sodium carbonate, in a solvent such as DMF or toluene at about 100° C.

Boronic acid derivatives II are obtainable from triflates IVa by treatment with the appropriate boron reagent, such as bis(neopentyl glycolato)diboron:

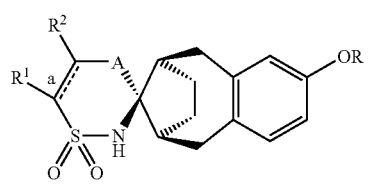

(a) R = Tf
(b) R = CH₂Ph where Tf represents trifluoromethanesulfonyl and A, a, $R^1$ and $R^2$ have the same meanings as before. The reaction takes place under similar conditions to the coupling of II and III.

Triflates IVa are obtainable by hydrogenation of the corresponding benzyl ethers IVb and treatment of the resulting phenols with triflic anhydride. The hydrogenation can be carried out in methanolic solution over a Pd/C catalyst, and reaction with triflic anhydride is conveniently effected in pyridine at 0° C.

Compounds IVb in which $R^1$ does not complete a ring and bond a is double may be obtained by cyclisation of vinyl sulfonamides V:

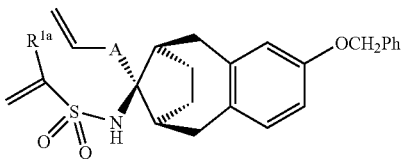

where $R^{1a}$ is $R^1$ that does not complete a ring and A has the same meaning as before. Preferably, $R^{1a}$ is H. Typical cyclisation conditions involve treatment with Grubbs II catalyst in toluene at about 80° C.

Corresponding compounds in which bond a is single are obtained by hydrogenation of the compounds in which bond a is double. Suitable conditions are the same as for cleavage of the benzyl ethers in IVb, and both processes are typically carried out simultaneously.

Compounds of formula IVb in which bond a is single and $R^1$ is alkyl are most conveniently obtained by alkylation of the corresponding compounds in which $R^1$ is H. Alternatively, such an alkylation may be performed on the appropriate compound of formula I as a final step.

Compounds V are obtainable by hydrolysis of sulfinamides VI to the corresponding amines and treatment of same with $ClCH_2CH(R^{1a})SO_2Cl$:

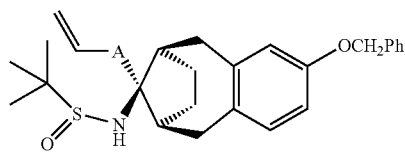

VI where A and $R^{1a}$ have the same meanings as before. The hydrolysis may be carried out using methanolic HCl and the reaction with the chloroethanesulfonyl chloride takes place in the presence of a base such as pyridine in an inert solvent such as dichloromethane at about 0° C.

Compounds VI are obtained by reaction of imine VII with Grignard reagents VIII:

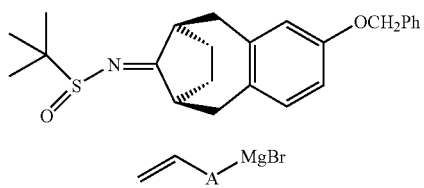

VII

VIII where A has the same meaning as before. The reaction takes place at 0° C. to ambient temperature in an aprotic solvent such as dichloromethane.

An alternative route to compounds IVb involves hydrolysis of sulfinamides IX followed by cyclisation of the resulting amines:

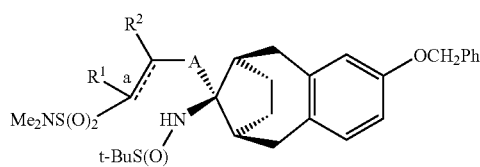

IX where A, a, $R^1$ and $R^2$ have the same meanings as before. The hydrolysis may be carried out as described above in connection with compound VI, and cyclisation may be effected by refluxing in pyridine. This is the preferred method in the case that A is a bond and $R^1$ and $R^2$ complete a fused benzene ring. Compounds IX in which A is a bond and $R^1$ and $R^2$ complete a fused benzene ring are obtainable by reaction of imine VII with N,N-dimethylbenzenesulfonamide, for example in the presence of BuLi and $AlMe_3$ in toluene at −78° C.

Imine VII is obtainable by condensation of ketone Xa with t-butylsulfinamide in the presence of $Ti(OEt)_4$ in refluxing tetrahydrofuran:

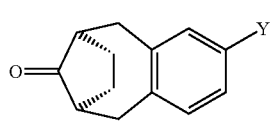

X (a) Y = $OCH_2Ph$
(b) Y = $NH_2$
(c) Y = $CO_2C_{1-4}alkyl$

Examples of compounds Ar—X—L suitable for reaction with boronates II include pyrazoles XI:

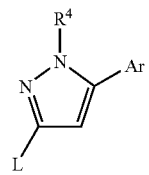

XI where $R^4$ is $C_{1-6}$alkyl, optionally bearing up to 3 halogen substituents, and Ar and L have the same meanings as before. Compounds XI in which L is triflate or nonaflate are accessible from the reaction of alkynes Ar—C≡C—$CO_2$Me with $R^4NHNH_2$ and treatment of the resulting pyrazolones with triflic anhydride or nonafluorobutanesulfonyl fluoride respectively. Compounds XI in which L is Br are available by reaction of nonaflates XII with ArZnBr:

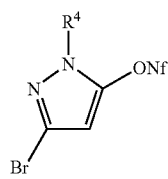

XII where Nf represents nonafluorobutanesulfonyl, and Ar and $R^4$ have the same meaning as before.

Further examples of compounds Ar—X—L include bromoimidazoles XIII:

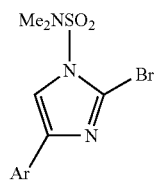

XIII where Ar has the same meaning as before. After coupling with boronates II, removal of the dimethylaminosulphonyl protecting group (e.g. by reflux in a mixture of THF and hydrochloric acid) then provides a compound of formula I in which Ar—X- represents a 4-substituted-1H-imidazol-2-yl moiety.

Other notable examples of compounds Ar—X—L which may similarly undergo coupling via boronates II include 4-bromo-1-(Ar-substituted) imidazoles and 3-bromo-1-(Ar-substituted)-1,2,4-triazoles, where Ar has the same meaning as before.

When the group X comprises an NH functionality in the ring (as in imidazole, for example), reaction of boronic acid II ($R^3$=H) with Ar—X—H provides compounds of formula I in which X is bonded to the fused benzene ring through nitrogen. The reaction takes place at ambient temperature in dichloromethane in the presence of di-□-hydroxo-bis(N,N, N',N'-tetramethylethylenediamine)copper(II) chloride.

Alternatively, the Ar—X moiety may be assembled in a three-stage process in which firstly an HX- group is introduced by reaction of boronate II with HX-L, where L and X have the same meanings as before; secondly, the resulting product is brominated to convert the HX- group to Br—X-; and thirdly, reaction with Ar—B($OR^3$)$_2$ provides a compound of formula I, where Ar and $R^3$ have the same meanings as before.

It will be apparent that the steps described above may be carried out in a different order. Thus, ketone Xa may be converted to the corresponding triflate and thence to the corresponding boronate as described for the conversion of IVb to II, then coupled with Ar—X—L prior to construction of the spiro-linked cyclic sulfonamide moiety by the methods described above.

Alternatively, aniline derivatives Xb and carboxylates Xc may serve as starting materials for the construction of the relevant heteroaryl moieties —X—Ar using conventional synthetic routes.

It is emphasised that the above formulae II, IV-VII, IX and X represent both of the enantiomeric forms arising from the overall asymmetry of the molecules, either singly or in mixtures of any proportion.

It will also be appreciated that where more than one isomer can be obtained from a reaction then the resulting mixture of isomers can be separated by conventional means.

Where the above-described process for the preparation of the compounds according to the invention gives rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as di-p-toluoyl-D-tartaric acid or di-p-toluoyl-L-tartaric acid, followed by fractional crystallization and regeneration of the free base. The novel compounds may also be resolved by formation of diastereomeric esters or amides, followed by chromatographic separation and removal of the chiral auxiliary. Alternatively, such techniques may be carried out on racemic synthetic precursors of the compounds of interest.

In a preferred route to enantiomerically pure compounds of formula I, racemic intermediate Xa or the corresponding phenol is subjected to preparative chiral HPLC to provide the corresponding homochiral intermediate, which is then converted to homochiral compounds of formula I by the routes indicated above.

Alternatively, intermediate Xb is resolved via salt formation with (+) or (−) mandelic acid. The resulting homochiral aniline is converted to the corresponding phenol (via the corresponding diazonium salt) and thence to the homochiral benzyl ether Xa, which may then be converted to homochiral compounds of formula I by the methods outlined above.

Where they are not commercially available, the starting materials and reagents used in the above-described synthetic schemes may be prepared by conventional means. The ketones X may be prepared by the method described in *J.Org.Chem.*, 47, 4329-34, 1982 or analogues thereof.

During any of the above synthetic sequences it may be necessary and/or desirable to protect sensitive or reactive groups on any of the molecules concerned. This may be achieved by means of conventional protecting groups, such as those described in Protective Groups in Organic Chemistry, ed. J.F.W. McOmie, Plenum Press, 1973; and T.W. Greene & P.G.M. Wuts, Protective Groups in Organic Synthesis, John Wiley & Sons, 1991. The protecting groups may be removed at a convenient subsequent stage using methods known from the art.

An assay which can be used to determine the level of activity of compounds of the present invention is described in WO01/70677. A preferred assay to determine such activity is described in WO02/081435. See also *Biochemistry*, 2000, 39(30), 8698-8704 and *J.Neuroscience Methods*, 2000, 102, 61-68.

The compounds of the invention show unexpectedly high affinities as measured by one or more of the above assays. Thus, the following examples all had an $ED_{50}$ of less than 50 nM, typically less than 10 nM, and in preferred cases less than 5 nM in at least one of the above assays. In general, the compounds also show good oral bioavailability and/or brain penetration.

The following examples illustrate the invention.

EXAMPLE 1

Intermediate A

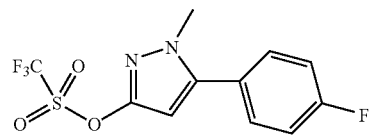

To a solution of methyl 4-(fluorophenyl)propynoate (J. Org. Chem. 1987, 52(16), 3662-8) (13 g, 73 mmol) in methanol (60 ml) was added water (60 ml) followed by methylhydrazine (4 ml, 77 mmol), the mixture was stirred for 6 hrs at 60° C. then left to stand overnight. The solid was filtered and washed with water then a minimum volume of methanol and dried overnight, affording 7.7 g of 5-(4-fluorophenyl)-1-methyl-1,2-dihydropyrazol-3-one (55%).

To a cooled suspension of the above pyrazolone (15.5 g, 81 mmol) in dry pyridine (100 ml) was added in three portions trifluoromethanesulfonic anhydride (24 g, 85 mmol) maintaining the temperature below 5° C. The cooling bath was then removed and the reaction was stirred for two hours before pouring into 2M hydrochloric acid and extracting into ethyl acetate. The organic layer was washed with brine, saturated sodium hydrogen carbonate, and dried (sodium sulphate), filtered and evaporated to yield a residue which was dissolved in toluene and evaporated and then dissolved in isohexane and filtered through a plug of silica, eluting with dichloromethane. The solvent was evaporated to yield product as a colourless oil (23.4 g, 89%).

Intermediate B

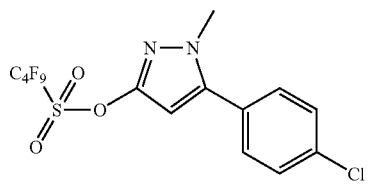

Prepared as for Intermediate A, using methyl 4-chlorophenylpropynoate in the first step, and nonafluorobutanesulfonyl fluoride in the second step.

EXAMPLE 1 (RACEMIC)

Step 1:

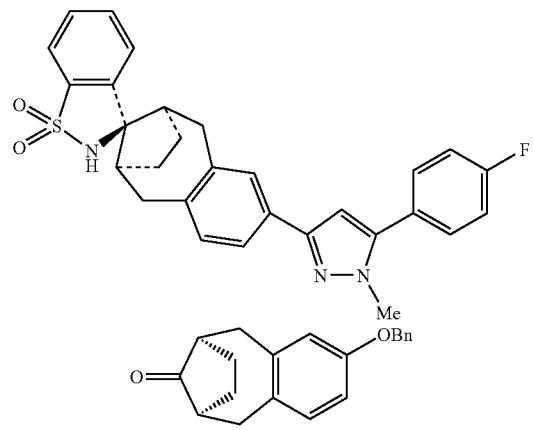

A mixture of 2-hydroxy-5,6,7,8,9,10-hexahydro-6,9-methanobenzo[α][8]annulen-11-one (15 g; J. Org. Chem 1982, 47, 4329), $K_2CO_3$ (20.5 g) and benzyl bromide (10.6 ml) in DMF (100 ml) was stirred for 48 hrs at room temperature. The reaction was diluted with water (500 ml) and extracted with EtOAc (3×150 ml). The combined organic phases were washed with water (2×300 ml), brine (150 ml), dried and concentrated to give a gummy oil which crystallized on standing and after trituration with ether gave the title benzyl ether (19.5 g, 90%) as a white solid. δ ($^1$H, 360 MHz, $CDCl_3$) 1.32 (2H, m), 1.85 (2H, m), 2.57 (2H, m), 2.87 (4H, m), 5.05 (2H, s), 6.82 (2H, m), 7.11 (1H, d, J=8.2 Hz), 7.37 (5H, m).

Step 2:

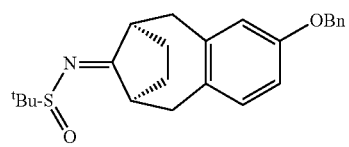

A solution of the product from Step 1 (20 g, 68 mmol), (+/−)tert-butyl sulfinamide (9.2 g, 76 mmol) and titanium (IV) ethoxide (tech., 29.2 mL, 140 mmol) in dry THF (140 mL) was stirred and heated at reflux under nitrogen for 4 hours. The reaction was allowed to cool to room temperature and poured into rapidly stirred brine (160 mL). The mixture was stirred for 20 minutes, then filtered through Hyflo™, washing with ethyl acetate. The filtrate was transferred to a separating funnel. The layers were separated, and the aqueous layer was extracted with ethyl acetate (×1). The combined organic extracts were washed with brine, then dried ($Na_2SO_4$), filtered and evaporated. The residue was purified by chromatography on silica, eluting with 20→30% ethyl acetate/hexanes, to give the imine (24.9 g, 93%) as a colourless solid. MS (ES+) 396 ([MH]$^+$).

Step 3

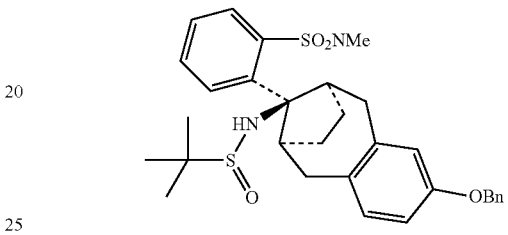

n-Butyllithium (1.6M, 1.6 mL, 2.5 mmol) was added dropwise at 0°C to a stirred solution of N,N-dimethylbenzenesulfonamide (0.46 g, 2.5 mmol) in dry toluene (4 mL) under $N_2$. The yellow suspension was stirred at 0°C for 30 min, then cooled to −78° C. Meanwhile, trimethylaluminium (2M in toluene, 0.70 mL, 1.4 mmol) was added at −78° C. to a stirred solution of the sulfinylimine from Step 2 (0.50 g, 1.26 mmol) in dry toluene (2 mL) under $N_2$. The solution of the sulfonamide anion was added at −78°C to the trimethylaluminium/sulfinylimine complex. After 2 h, the mixture was warmed to 0° C. After a further 1.5 h, the mixture was warmed to rt and stirred for 18 h. The reaction was quenched by addition of sat. aq. sodium sulfate until effervescence ceased. Solid sodium sulfate and ethyl acetate (50 mL) were added and the mixture was filtered and concentrated. Chromatography, eluting with 25% then 80% ethyl acetate-isohexane, gave the sulfinamide as a white foam (0.263 g, 36%).

Step 4

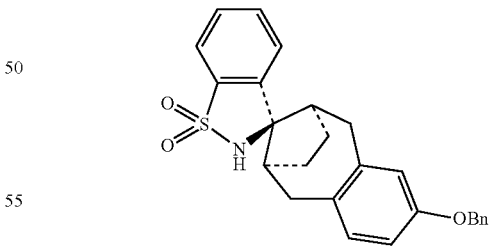

A solution of HCl in diethyl ether (1M, 1.5 mL) was added to a solution of the sulfinamide from Step 3 (0.26 g, 0.45 mmol) in methanol (1 mL) at rt. After 1.5 h, the mixture was poured into sodium hydrogencarbonate (80 mL) and extracted with ethyl acetate (50 mL). The extract was dried with sodium sulfate and concentrated. The material was dissolved in pyridine (5 mL) and refluxed under $N_2$ for 24 h. The solvent was removed by evaporation. The residue was dissolved in ethyl acetate (20 mL), and washed with 1M HCl (20 mL). The organic layer was dried over sodium sulfate and concentrated to give the cyclic sulfonamide as an off-white powder (0.152 g, 78%).

Step 5

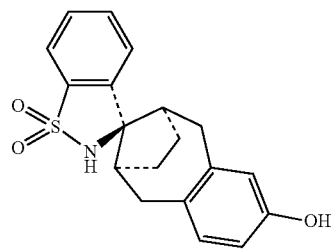

A mixture of the benzyl ether from Step 4 (0.09 g, 0.21 mmol), ammonium formate (1.0 g) and 10% Pd—C (0.1 g) in methanol (10 mL) was refluxed for 3 h. The cooled mixture was filtered and concentrated. The residue was redissolved in ethyl acetate (20 mL) and washed with water (20 mL), dried over sodium sulfate and concentrated to give the phenol as a white solid (0.054 g, 75%).

Step 6

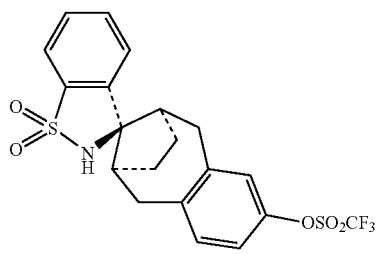

Trifluoromethanesulfonic anhydride (0.04 mL, 0.24 mmol) was added to a stirred solution of the phenol from Step 5 (0.054g, 0.158 mmol) in pyridine (2 mL) at 0° C. under $N_2$. After 3 h, the mixture was poured into 1 M HCl (40 mL). The yellow precipitate was collected, redissolved in ethyl acetate and filtered through a plug of silica gel. The filtrate was concentrated to give the triflate as a yellow solid (0.067 g, 89%).

Step 7

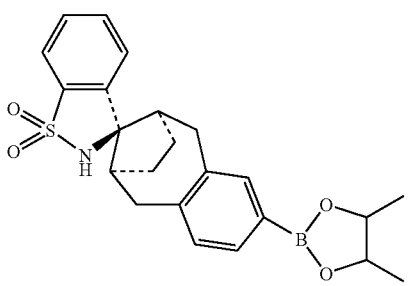

A solution of the triflate from Step 6 (0.067 g, 0.141 mmol), bis(pinacolato)diboron (0.04 g, 0.16 mmol), dppf (0.008 g), $PdCl_2$dppf (0.012 g) and potassium acetate (0.04 g, 0.42 mmol) in DMF (2 mL) was degassed and flushed with $N_2$, then stirred at 100° C. for 2 h. The solution was diluted was water (30 mL) and extracted with ethyl acetate (10 mL). The extract was dried over sodium sulfate and concentrated. Chromatography, eluting with 30% then 40% ethyl acetate-isohexane, gave the boronate as a white foam (0.061 g, 96%).

Step 8

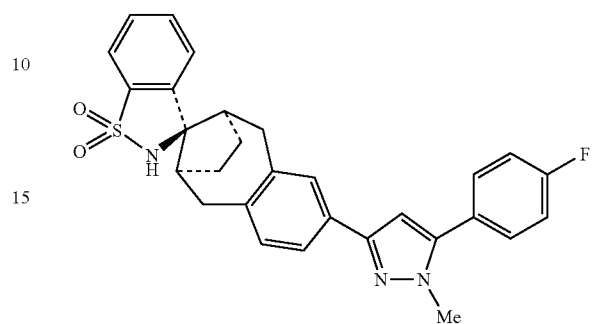

A solution of the boronate from Step 7 (0.06 g, 0.133 mmol), Intermediate A (0.043 g, 0.133 mmol), $Pd(PPh_3)_4$ (0.06 g), potassium carbonate (0.066 g, 0.67 mmol) in water (0.05 mL), toluene (1 mL) and ethanol (0.5 mL) was irradiated in the microwave at 100° C. for 20 min. The mixture was diluted with water (10 mL) and extracted with ethyl acetate (10 mL). The extract was dried over sodium sulfate and concentrated. Chromatography, eluting with 40% ethyl acetate-isohexane, gave an off-white powder (0.018 g, 27%).

EXAMPLE 2 (HOMOCHIRAL)

Step 1

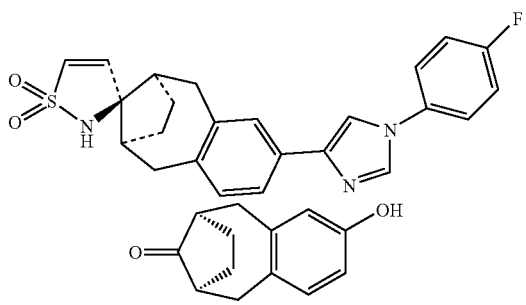

2-Hydroxy-5,6,7,8,9,10-hexahydro-6,9-methanobenzo [α][8]annulen-11-one (J. Org. Chem 1982, 47, 4329) was resolved using a Berger SFC semi-preparative instrument (chiralpak AS (25×2 cm, 20 um); 15% MeOH/$CO_2$@50 mL/min; 35° C.; 100 bar; second eluted enantiomer).

Step 2

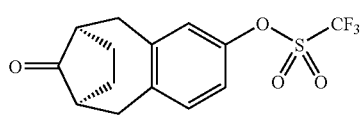

To a stirred solution of the product from Step 1 (6.83 g, 34 mmol) in dry DCM (40 mL) at 0° C under nitrogen was added pyridine (3.8 mL, 47 mmol) followed by triflic anhydride (8.0 mL, 47 mmol). The reaction was stirred at 0° C. for 2 hours. Water (40 mL) was added and the layers were separated. The aqueous layer was extracted with DCM (x2). The combined extracts were washed with brine (x1), then dried (MgSO₄), filtered and evaporated. The residue was purified by chromatography on silica, eluting with 10-15% EtOAc/hexane, to give the triflate (9.64g, 85%). (400 MHz ¹H, δ-CDCl₃) 1.28 (2H, m) 1.92 (2H, m), 2.64 (2H, m), 2.85-3.05 (4H, m), 7.13 (2H, m), 7.29 (1H, m).

Step 3

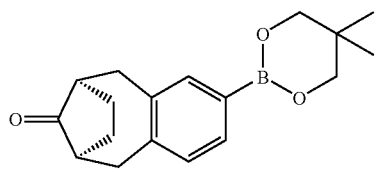

A solution of the triflate from Step 2 (2.546 g, 7.6 mmol), bis(neopentyl glycolato)diboron (2.064 g, 9.1 mmol) and KOAc (1.495 g, 15.2 mmol) in dioxane (27 mL) and DMSO (3 mL) was deoxygenated by bubbling nitrogen through the solution for 20 minutes. [1,1'-Bis (diphenylphosphino)ferrocene] palladium (II) chloride (0.622 g, 0.76 mmol) was added and deoxygenation was continued for a further 10 minutes. The reaction was heated at 90° C. for 16 hours, then allowed to cool and diluted with water (40 mL). The reaction was extracted with EtOAc (x3). The combined extracts were washed with water then brine, dried (MgSO₄), filtered and evaporated. The residue was purified by chromatography on silica, eluting with 20% EtOAc/hexane to give the product (1.881 g, 83%). (360MHz ¹H, δ-CDCl₃) 1.04 (6H, s), 1.30 (2H, m), 1.83 (2H, m), 2.59 (2H, m), 2.85-3.00 (4H, m), 3.78 (4H, s) 7.19 (1H, m) 7.62 (2H, m).

Step 4

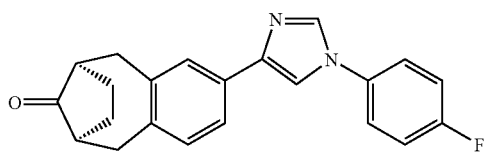

A solution of the boronate from Step 3 (1.787 g, 6.0 mmol), 4-bromo-1-(4-fluorophenyl)-1H-imidazole (1.589 g, 6.6 mmol), and cesium carbonate (4.296 g, 13.2 mmol) in DME (20 mL) and water (10 mL) was deoxygenated by bubbling nitrogen through the solution for 30 minutes. Tetrakis (triphenylphosphine) palladium (0) (0.693 g, 0.6 mmol) was added and deoxygenation was continued for a further 10 minutes. The reaction was heated at 90° C. for 16 hours then allowed to cool and diluted with water (40 mL). The catalyst was removed by filtration through Hyflo® and the filtrate was extracted with EtOAc (x3). The combined extracts were washed with water then brine, dried (MgSO₄), filtered and evaporated. The residue was purified by chromatography on silica, eluting with 40% EtOAc/hexane.

The resulting solid was washed with ether to give the product (1.818 g, 88%). (360MHz ¹H, δ-CDCl₃) 1.36 (2H, m), 1.87 (2H, m), 2.61 (2H, m), 2.89-3.09 (4H, m), 7.23 (3H, m), 7.42 (2H, m) 7.51 (1H, s), 7.62 (1H, m), 7.73 (1H, s), 7.83 (1H, s).

Step 5

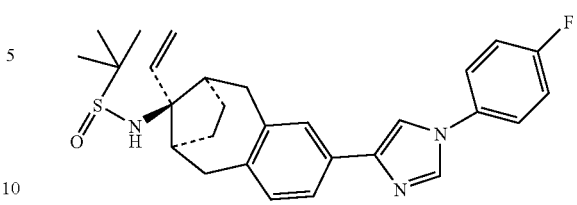

The product of Step 4 was treated with t-butylsulfinamide as described in Example 1 Step 2. Vinylmagnesium bromide (1M, THF, 10 mL) was added at 0° C. to a stirred solution of the resulting sulfinylimine (3.11 g, 6.93 mmol) in dry dichloromethane (30 mL). The mixture was warmed to rt and stirred for 16 h. The mixture was poured into water (100 mL). IM citric acid (20 mL) and sat. aq. sodium hydrogencarbonate (10 mL) were added. The mixture was extracted with dichloromethane-methanol (9:1, 2×100 mL). The extracts were dried over sodium sulfate and concentrated. Chromatography, eluting with ethyl acetate gave the sulfinimide as an orange foam (2.72, 83%).

Step 6

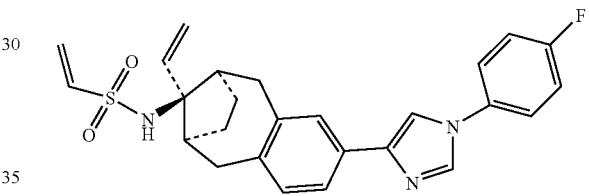

A solution of the sulfinamide from Step 5 (0.78 g, 1.63 mmol) and 1M HCl in diethyl ether (4 mL) in methanol (10 mL) was stirred at rt for 25 h. The solution was poured into sat. aq. sodium hydrogencarbonate (100 mL) and extracted with ethyl acetate (2×50 mL). The extracts were washed with water (50 mL), brine (20 mL), dried over sodium sulfate and concentrated to give a gum. The material was redissolved in pyridine (10 mL) and dichloromethane (10 mL) and stirred at 0° C. 2-Chloroethanesulfonyl chloride (0.2 mL, 1.0 mmol) was added dropwise. After stirring at rt for 18 h the mixture was diluted with 1M citric acid (100 mL) and extracted with dichloromethane-methanol (9:1, 2×100 mL). The extracts were washed with water (50 mL) and brine (20 mL, dried over sodium sulfate and concentrated. Chromatography, eluting with 50% then 100% ethyl acetate-isohexane, gave the sulfonamide as a pink solid (0.349 g, 46%).

Step 7

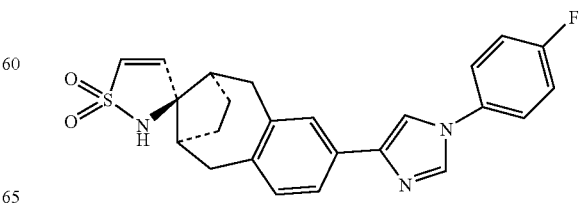

A solution of the sulfonamide from Step 2 (0.349 g, 0.754 mmol) and Grubbs II catalyst (0.04 g) in dry toluene (35 mL) was degassed and flushed with N₂. The solution was stirred at 80° C. for 20 h. The solution was filtered through a plug of silica gel and concentrated. Preparative normal-phase HPLC, eluting with ethyl acetate-isohexane, gave recovered starting material (0.131 g, 38%) and the cyclic sulfonamide (0.072 g, 22%).

EXAMPLE 3 (HOMOCHIRAL)

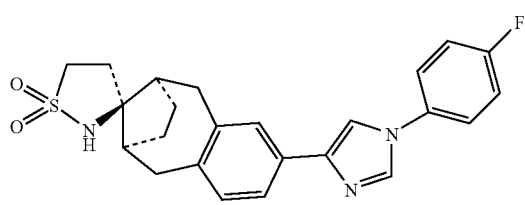

Sodium borohydride (0.01 g, 0.26 mmol) was added at 0° C. to a stirred solution of the product of Example 2 (0.036 g, 0.083 mmol) in dichloromethane (2 mL), ethanol (2 mL) and water (0.5 mL). After 2 h further sodium borohydride (0.01 g) was added. After a further 2 h, the solution was partitioned between water (50 mL) and dichloromethane (2×30 mL). The organic extracts were washed with brine (25 mL), dried over sodium sulfate and concentrated to give the sulfonamide as a white powder (0.03 g, 83%).

EXAMPLE 4 (MIXTURE OF 2 DIASTEREOISOMERS)

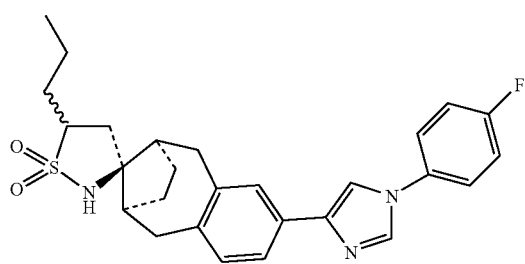

A solution of sodium hexamethyldisilylazide (1M, THF, 0.075 mL) was added to a stirred solution of the product of Example 3 (0.03 g, 0.069 mmol) in dry THF (2 mL) at rt under N₂. After 5 min, chloromethyl methyl ether (0.007 mL, 0.075 mmol) was added. After 16 h, the mixture was diluted with water (3 mL) and extracted with dichloromethane (3×3 mL). The extracts were dried and concentrated to give the MOM-protected sulfonamide as a yellow solid (0.028 g). The material was redissolved in dry THF (0.5 mL) and a solution of sodium hexamethyldisilylazide (1M, THF, 0.1 lmL) was added. After 1 h, 1-bromopropane (0.05 mL) was added. After 2 h, further sodium hexamethyldisilylazide (1M, THF, 0.05 mL) was added, followed by 1-bromopropane (0.05 mL) after 1 h. After a further 2 h, the mixture was diluted with water (5 mL) and extracted with ethyl acetate (3×5 mL). The extracts were dried over sodium sulfate and concentrated. Preparative reverse-phase HPLC, eluting with acetonitrile-water, gave alkylated material (0.004 g). The material was dissolved in methanol (1 mL) and water (0.2 mL) and trifluoroacetic acid (0.2 mL) was added. After 2 h the solution was evaporated to dryness. Preparative reverse-phase HPLC, eluting with acetonitrile-water, gave the sulfonamide (1:1 mixture of 2 diastereoisomers) as a white solid (0.003 g, 12%).

EXAMPLE 5 (MIXTURE OF 2 DIASTEREOISOMERS)

Step 1

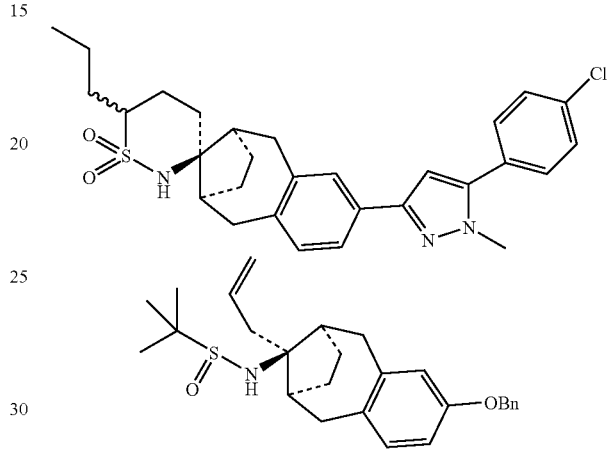

The homochiral phenol from Example 2 Step 1 was reacted with t-butylsulfinamide as described in Example 1 Step 2. The resulting homochiral sulfinylimine was treated with allylmagnesium bromide using the method described in Example 2, Step 5.

Step 2

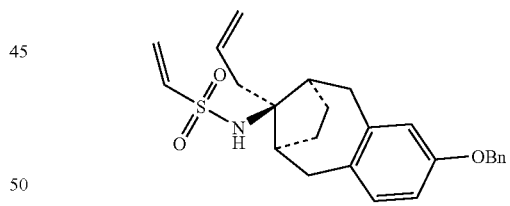

Prepared from the sulfinamide from Step 1 using the method described in Example 2, Step 6. Straw-coloured syrup (53%).

Step 3

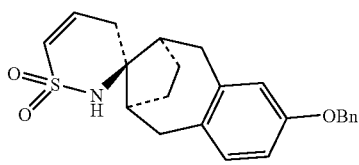

Prepared from the sulfonamide in Step 2 using the method described in Example 2, Step 7. Beige solid (93%).

Step 4

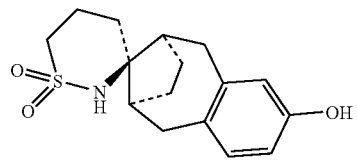

A solution of the sulfonamide from Step 3 (0.50 g, 1.26 mmol) in ethyl acetate (10 mL) and methanol (10 mL) was hydrogenated at 40 psi $H_2$ over 10% Pd—C (0.5 g) for 24 h. The catalyst was removed by filtration and the filtrate was concentrated. The resulting solid was rinsed with ethyl acetate-diethyl ether (1:9) and dried to give the phenol as a beige solid (0.313 g, 81%).

Step 5

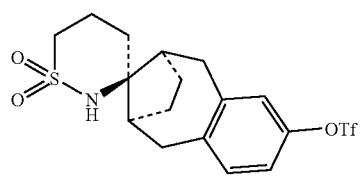

Prepared from the phenol in Step 4 using the method described in Example 1, Step 6 White foam (78%).

Step 6

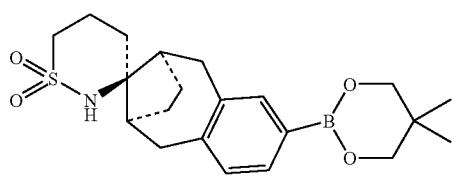

Prepared from the triflate Step 5, using the method described in Example 1, Step 7 replacing bis(pinocolato) diboron with bis(neopentylglycolato)diboron. While solid (47%).

Step 7

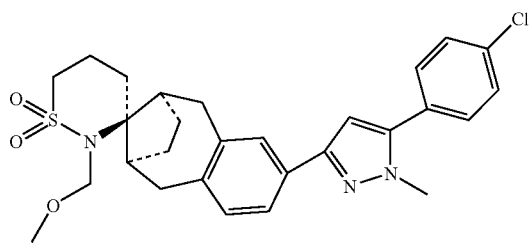

A solution of the boronate from Step 6 (0.146 g, 0.36 mmol), Intermediate B (0.02 g, 0.41 mmol), $Pd(PPh_3)_4$ (0.04 g) and sodium carbonate (0.076 g, 0.72 mmol) in dry DMF was stirred at 100° C. under $N_2$ for 24 h. The mixture was partitioned between 1M HCl (20 mL) and ethyl acetate (20 mL). The organic layer was dried over sodium sulfate and concentrated. Chromatography, eluting with 33% then 50% ethyl acetate-isohexane, gave a white foam. The material was suspended in dry THF (1 mL) at rt under $N_2$ and sodium hexamethyldisilylazide (1M, THF, 0.2 mL) was added, followed by chloromethyl methyl ether (0.015 mL, 0.2 mmol). After stirring for 18 h, the suspension was diluted with water (10 ml) and extracted with ethyl acetate (2×10 mL). The extracts were dried over sodium sulfate and concentrated. Chromatography, eluting with 20% then 40% ethyl acetate-isohexane, gave the protected sulfonamide as a white powder (0.023 g, 12%).

Step 8

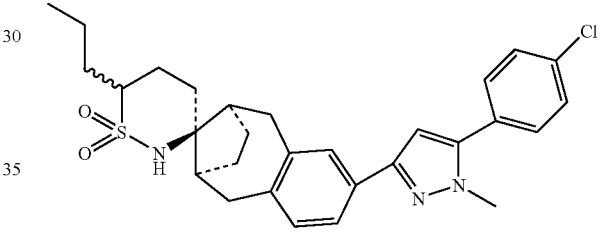

A solution of potassium hexamethyldisilylazide (0.5 M, toluene, 0.14 mL) was added to a stirred solution of the sulfonamide from Step 7 (0.023 g, 0.044 mmol) in dry THF (1 mL) at rt under $N_2$. 1-Iodopropane (0.01 mL, 0.1 mmol) was added. After 18 h, further potassium hexamethyldisilylazide (0.5 M, toluene, 0.14 mL) and 1-iodopropane (0.02 mL) were added. After a further 20 h, the reaction was diluted with 1M HCl (10 mL) and extracted with ethyl acetate (2×10 ML). The extracts were dried over sodium sulfate and concentrated. Preparative reverse-phase HPLC, eluting with acetonitrile-water, gave the alkylated sulfonamide (1:1 mixture of diastereoisomers). The material was redissolved in methanol (2 mL) and dichloromethane (0.5 mL) and trifluoroacetic acid (0.5 mL) was added. After standing for 1 h at rt the mixture was concentrated to dryness. Preparative reverse-phase HPLC, eluting with acetonitrile-water, gave the deprotected sulfonamide as a white solid (0.004 g, 17%).

What is claimed is:

1. A method of treating a patient for Alzheimer's Disease, comprising administering to the patient an effective amount of a compound selected from:

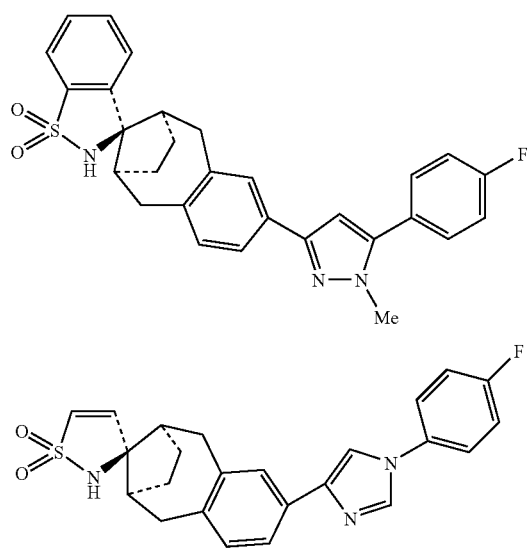
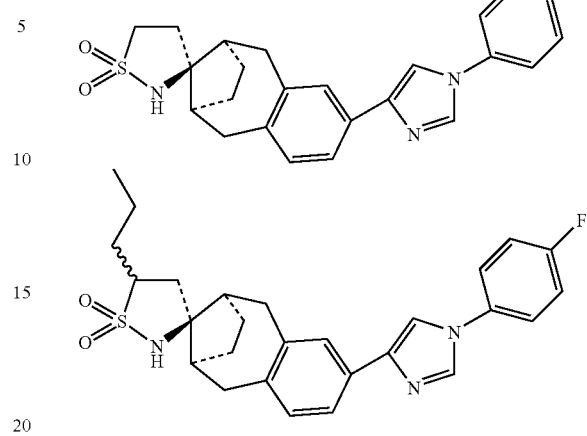
or a pharmaceutically acceptable salt thereof.
* * * * *